United States Patent [19]
Kalloo et al.

[11] Patent Number: 5,846,567
[45] Date of Patent: Dec. 8, 1998

[54] CLOT DISSOLVING METHOD

[75] Inventors: Anthony N. Kalloo, Glenn Dale; Pankaj Jay Pasricha, Columbia, both of Md.

[73] Assignee: Chek-Med Systems, Inc., Camp Hill, Pa.

[21] Appl. No.: 840,783

[22] Filed: Apr. 16, 1997

[51] Int. Cl.$^6$ .................................................. A61K 33/40
[52] U.S. Cl. ............................................ 424/616; 514/834
[58] Field of Search .............................. 424/616; 514/834

[56] References Cited

U.S. PATENT DOCUMENTS

| | | |
|---|---|---|
| 3,903,265 | 9/1975 | Meisch . |
| 4,198,390 | 4/1980 | Rider . |
| 4,477,438 | 10/1984 | Willcockson et al. ................... 424/616 |
| 5,104,644 | 4/1992 | Douglas ................................... 424/616 |

OTHER PUBLICATIONS

Hankin, et al., "Hydrogen Peroxide as a Topical Hemostatic Agent", *Clinical Orthopaedics and Related Research,* 1984 Jun.: (186):244–8.

Kalloo, et al., "Taking the Red Out of Bleeding Lesions: Improved Visualization and Clot Dissolution With Hydrogen Peroxide Spray", *Gastrointestinal Endoscopy* 1996 Apr.(43): Abstract 27 (Issue mailed Apr. 18, 1996).

*The Merck Index,* 12th Edition, Merck & Co., Inc., Whitehouse Station, NJ, 1996, entries 3264 and 4839.

*USP Dictionary of USAN and International Drug Names,* U.S. Pharmacopeia, Rockville, M.D., 1996, pp. 354 and 652.

*Primary Examiner*—Leonard Schenkman
*Attorney, Agent, or Firm*—Eugene Chovanes

[57] ABSTRACT

A method, composition and kit for effecting hemostasis of a bleeding point and/or dissociating an adherent blood clot at a lesion site on an internal organ, include a composition comprising hydrogen peroxide and surfactant. The composition is applied to the site thereby effecting hemostasis and clot dissociation and clearing the field for endoscopy.

10 Claims, No Drawings

CLOT DISSOLVING METHOD

The invention relates to effecting hemostasis of bleeding points on internal bodily organs and the dissociation of adherent blood clots on internal body organs, particularly on mucosal surfaces.

BACKGROUND OF THE INVENTION

Bleeding points can occur on internal organs, such as the esophagus, stomach, small intestine, large intestine and bladder, through a number of etiologies. Ulcers are a major causation, but bleeding lesions of other types occur on internal organs, especially in the alimentary canal. These lesions include, for example, hemorrhagic gastritis which is an erosive condition resulting in multiple bleeding points in the stomach, arteriovenous malformations often seen in the colon, diverticulosis bleeding occurring from herniations of the lining mucous membrane protruding through a defect in the muscular coat of a tubular internal organ and which occurs most commonly in the colon, Mallory Weiss tears of the esophagus that can occur with violent vomiting, dilatation of a stricture anywhere in the GI tract with resulting bleeding tear, and bleeding sites which unavoidably result from medical procedures such as sphincterotomy that is necessitated when a valve at the ampulla of Vater, where bile from liver and pancreas juices flow into the intestine, has narrowed and must be subjected an electrocautery cut in the manner of a surgical incision by the endoscopist. Bleeding points also occur on mucosal surfaces of other internal organs, for example, in hemorrhagic cystitis of the urinary bladder.

Particularly troublesome bleeding points occur at ulcers of the gastrointestinal tract. An ulcer is an inflammatory lesion generally resulting from local tissue necrosis, with loss or destruction of superficial tissue on the surface of an organ or tissue. For example, peptic ulcers occur in the mucous membrane of the esophagus, stomach or duodenum. By definition, ulcers extend through the muscularis mucosae and are usually over 5 mm in diameter.

One way of dealing with internal bleeding is with endoscopic management. In gastrointestinal bleeding, an endoscope is passed through the mouth and down into the GI tract for a visual assessment of the bleeding point. Endoscopic therapy, with a variety of hemostatic injection and coagulation techniques, can be used to treat bleeding points, often with epinephrine, ethanol or saline injection or heat application, e.g., using laser devices, electrocautery or heat probes.

A major problem in endoscopic management is the difficulty in identifying the bleeding source which is often obscured by overlying blood and clots. In the case of GI bleeding, ulcers with a visible vessel have a highly increased incidence of rebleeding and the appearance of the ulcer base is an important factor in assessing the probability of a rebleed. Traditional efforts at removing blood clots have been by lavage, e.g., using large bore gastric tubes, or by suction using large channel therapeutic endoscopes. These methods often fail to dislodge blood clots which are adherent to the base of the bleeding site. Another method is to remove clots mechanically with a snare. Physicians are generally reluctant to use this latter technique because of the danger of inducing bleeding.

These problems have led to the search for other ways to attain hemostasis and dissociation of blood clots on internal organs.

SUMMARY OF THE INVENTION

The present invention includes compositions, methods and kits for effecting hemostasis at bleeding points on internal organs and/or dissociation or dissolution of adherent blood clots on internal organs, such as in the alimentary canal of a mammal, preferably a human. The invention includes a hemostatic and clot dissociating composition comprising hydrogen peroxide and optionally a surfactant.

The invention also includes a method of effecting hemostasis at bleeding points on internal organs and/or dissociating adherent blood clots on surfaces of internal organs, such as in the gastrointestinal tract by applying to the bleeding point or clot, preferably at its base, an effective amount of a composition comprising hydrogen peroxide and optionally, a surfactant. The surfactant can be applied concurrently with the hydrogen peroxide or after the application of hydrogen peroxide.

A kit for this treatment method contains the composition comprising a solution of hydrogen peroxide, preferably at a weight percent from about 1.0% to about 10.0%, more preferably from about 3 or 3.5% to about 4%, and optionally a surfactant in an amount of from about 0.1% to about 10%, more preferably from about 1.0% to about 5.0%, with percentages based on 100% treatment composition. The kit can also contain means for administering the composition.

The invention has a number of advantages. For example, the hydrogen peroxide decomposes into water and oxygen leaving no toxic residue. Moreover, the hydrogen peroxide, in some undetermined way, enhances hemostasis at a bleeding site. Furthermore, clots are dislodged cleanly and in a very short period of time leaving a clear field of vision to assess or further treat a lesion.

DETAILED DESCRIPTION OF THE INVENTION

The invention effects hemostasis at a bleeding point, particularly on internal mucosal surfaces. By hemostasis is meant arresting bleeding so that it is brought under control by being reduced or stopped. By bleeding point is meant a site which is amenable to and treatable by topical application of the composition for hemostasis. For gushing bleeding sites such as in severe arterial hemorrhaging, measures more drastic than the method of the invention would be required. The invention also dissociates blood clots adherent to mucosal surfaces. By dissociate is meant to remove, dislodge or dissolve.

Mucous membrane lines body passages and cavities which communicate directly or indirectly with the exterior. The mucosa is the innermost layer of the gut wall consisting of three layers, the inner epithelium with digestive glands, the lamina propria, and the muscularis mucosa; the epithelium and lamina propria are together called the mucous membrane (mucous coat) or the whole mucosa can be called the mucous membrane. The alimentary canal or gut extends from mouth to anus where foodstuffs are ingested and digested and from which they are absorbed into the body. The urinary bladder is the musculomembranous sac, situated in the anterior part of the pelvic cavity, that serves as a reservoir for urine which it receives through the ureters and discharges through the urethra. The bladder also has a mucosa, as do the trachea and bronchi in the lungs, etc.

The composition, method and kit of the invention are used in the in vivo treatment of bleeding points and/or adherent clots on internal organs. The sites particularly amenable to treatment according to the invention are in the gastrointestinal or urinary tracts. The bleeding points include as non-limiting examples, a situs of hemorrhagic gastritis, arteriovenous malformation, diverticulosis, Mallory Weiss tears of the esophagus, dilatation of a stricture, surgical incision, hemorrhagic cystitis and gastrointestinal ulcer.

Although hydrogen peroxide has been used for topical disinfection, and surfactants such as simethicone have been used clinically as anti-foaming agents to relieve flatulence, there has been no suggestion to use these components to effect hemostasis or to dissociate adherent clots at bleeding points on internal organs.

The composition includes hydrogen peroxide and optionally, a surfactant. Hydrogen peroxide and methods for its manufacture are referenced in The Merck Index, 12th ed., Merck & Co. Inc., Whitehouse Station, N.J., 1996, at entry 4839. Hydrogen peroxide solution is preferably prepared in water at a concentration of about 1% to about 10% by weight, more preferably from about 3.0% to about 4.0% by weight.

Surfactants useful herein include any substantially non-irritating, biocompatible agent which reduces surface tension. Many such agents are well known in the art. By biocompatible is meant non-damaging to human or non-human tissue. The surfactant serves to reduce bubbling or effervescence which occurs as the hydrogen peroxide acts on the clot. The preferred surfactant is simethicone.

Simethicone (USP) is described in the USP Dictionary of USAN and International Drug Names, U.S. Pharmacopeia, Rockville, Md., 1997, at page 652, as a mixture of poly(dimethylsiloxane) and silicon dioxide. The poly(dimethylsiloxane) is $\alpha$-(trimethylsilyl)-$\omega$-methyl-poly[oxy(dimethylsilylene)]. The calculated average of dimethylsiloxane units in poly(dimethylsiloxane) is 200 to 350. See also The Merck Index, 12th ed. at entry 3264. Other characteristics of simethicone are described in these references.

The simethicone is preferably prepared from the USP or FDA acceptable 100% solution. The simethicone is diluted to a concentration preferably from about 0.1% to about 5.0% by weight, more preferably from about 0.5% to about 2.0% by weight. An optional dispersant may be added to aid in separating simethicone molecules in water.

The hydrogen peroxide and surfactant can be prepared together in the same solution, or can be prepared in separate solutions for consecutive application. When both components are prepared in the same solution, the preferred milieu is water. When the components are applied separately, the $H_2O_2$ is preferably in water solution and the surfactant such as simethicone is preferably dispersed in an aqueous solution, preferably water.

The compositions of this invention can be employed in admixture with conventional excipients, i.e., pharmaceutically acceptable organic or inorganic carrier substances suitable for solution, dispersion, suspension, or emulsion applications which do not deleteriously react with the active compounds. Suitable pharmaceutically acceptable carriers include, but are not limited to, water, salt solutions, vegetable oils, benzyl alcohols, polyethylene glycols, gelatin, fatty acid monoglycerides and diglycerides, fatty acid esters, polyvinyl pyrrolidone, merely to name a few. The pharmaceutical preparations can be sterilized and if desired, mixed with auxiliary agents, e.g., lubricants, preservatives, stabilizers, wetting agents, emulsifiers, salts for influencing osmotic pressure, coloring, and the like which do not deleteriously react with the active compounds. They can also be combined, where desired with other active agents, e.g., antibiotics or anti-microbial agents.

For topical application, liquid preparations are suitable, e.g., liquids, drops and sprays. In some instances, it may be desired to employ a compatible carrier having a dynamic viscosity greater than water. This may help adherence to the target point.

In the method of the invention, the composition can be applied to the site of a bleeding point and/or adherent blood clot, e.g., by squirting or spraying using a syringe and catheter. Hemostasis and/or dissociation of the blood clot can be accomplished using an effective amount of the composition, generally about 20 to 300 cc or with even greater or lesser amounts of the composition depending upon the lesion being treated. The effective amount can easily be determined by the skilled practitioner. The preferred mode of application is through known endoscopic techniques.

In another aspect of the invention, a kit is provided for use to effect hemostasis of bleeding points and/or dissociate blood clots adherent at internal mucosal surfaces, particularly in the gastrointestinal or urinary tract. The kit can be used as an adjunct to endoscopy. The kit includes the composition containing hydrogen peroxide solution and optionally surfactant. The components can be packaged as a single solution or as separate solutions in any desired amount, ranging, for example from 20 cc to 500 cc or more. The kit can also include a means for application such as a syringe and catheter suitable for use in endoscopy.

The following examples serve to illustrate the invention. The examples, however, are not intended in any way to limit the scope of the invention. All percentages are by weight.

EXAMPLE 1

Five male dogs (weight 25–30 Kg) were anticoagulated with heparin 10,000 units and multiple biopsies taken at the body of the stomach to induce bleeding lesions. Blood was allowed to accumulate. A 3% solution of $H_2O_2$ in water in an amount of about 100 cc's was then flushed through a 5 Fr catheter and the blood immediately became translucent. The previously biopsied sites (source of bleeding) were then clearly visualized. Any resulting effervescence was dispersed by simethicone (10% simethicone, Mylicon, Johnson & Johnson-Merck Consumer Pharmaceuticals Co., Ft. Washington, Pa.) diluted in the 3% $H_2O_2$ 10:1 so that simethicone was 1%. There was no mucosal damage observed endoscopically immediately and 24 hours later. Biopsies taken one hour later showed mild superficial gastritis. This demonstrates that $H_2O_2$ is safe to the gastric mucosa and effective for hemostasis and clot dissociation.

EXAMPLE 2

A bleeding duodenal ulcer in a patient was endoscopically observed to be 7 mm with a small clot on the base. Forceful water spray with a hand syringe did not dislodge the clot. A solution containing 3% $H_2O_2$ with about 1% simethicone as in Example 1 was applied to the base of the clot. The solution attacked the base where the clot was attached to the bleeding blood vessel, apparently a relatively small point. Within 1–2 minutes and with about 10–15 cc of the $H_2O_2$/simethicone solution, the attachment point appeared to dissolve and the clot dislodged allowing observation of the base, application of epinephrine injection and heat hemostasis. Additionally, the blood vessel in the base stopped bleeding confirming that the composition of the invention exhibits hemostatic action on bleeding points as well as acting on the overlying clot.

We claim:

1. A method for effecting hemostasis of a bleeding point and/or dissociating an adherent blood clot, at an endoscopically observable mucosal lesion site on an internal organ in a mammal, the method comprising applying to said site a composition comprising hydrogen peroxide, and applying to said site a composition comprising a surfactant, said hydrogen peroxide in an amount effective to bring about hemostasis and/or dissociate the blood clot.

2. The method of claim 1 wherein the applying is at the base of the clot.

3. The method of claim 1 wherein the mammal is a human.

4. The method of claim 1 wherein the mucosal lesion site is a situs of hemorrhagic gastritis, arteriovenous malformation, diverticulosis, Mallory Weiss tear of the esophagus, dilatation of a stricture, surgical incision, hemorrhagic cystitis or gastrointestinal ulcer.

5. The method of claim 4 wherein the mucosal lesion site is the situs of a gastrointestinal ulcer.

6. The method of claim 1 wherein the surfactant is simethicone.

7. The method of claim 1 wherein the surfactant is applied concurrently with or after the application of hydrogen peroxide.

8. The method of claim 1 wherein the composition comprises surfactant in an amount of from about 0.1% to about 10.0% by weight.

9. The method of claim 1 wherein the composition comprises hydrogen peroxide in an amount of from about 1.0% to about 10.0% by weight.

10. The method of claim 1 wherein the hydrogen peroxide and the surfactant are applied concurrently in the same composition or are applied separately in separate compositions.

* * * * *